United States Patent [19]

Tanaka et al.

[11] Patent Number: 5,100,933
[45] Date of Patent: Mar. 31, 1992

[54] COLLAPSIBLE GEL COMPOSITIONS

[75] Inventors: Toyoichi Tanaka, Newton; Izumi Nishio, Somerville; Shao-Tang Sun, Arlington, all of Mass.

[73] Assignee: Massachusetts Institute of Technology, Cambridge, Mass.

[21] Appl. No.: 470,977

[22] Filed: Jan. 26, 1990

Related U.S. Application Data

[63] Continuation of Ser. No. 846,645, Mar. 31, 1986, abandoned, which is a continuation of Ser. No. 712,459, Mar. 15, 1985, abandoned, which is a continuation of Ser. No. 658,075, Oct. 5, 1984, abandoned, which is a continuation of Ser. No. 473,161, Jan. 28, 1983, abandoned.

[51] Int. Cl.$^5$ ............................................. C08J 3/28
[52] U.S. Cl. ....................................... 523/300; 524/555
[58] Field of Search ................... 524/364, 379, 555; 523/300

[56] References Cited

U.S. PATENT DOCUMENTS

| | | | |
|---|---|---|---|
| 2,831,841 | 4/1958 | Jones | 526/287 |
| 3,247,171 | 4/1966 | Walker et al. | 525/329.4 |
| 3,993,553 | 11/1976 | Assarsson et al. | 523/300 |
| 4,004,997 | 1/1977 | Tsukamoto et al. | 523/300 |
| 4,172,066 | 10/1979 | Zweigle et al. | 525/329.4 |

FOREIGN PATENT DOCUMENTS 0124188 11/1974 Japan ............................ 525/329.4

OTHER PUBLICATIONS

Tanaka, et al., *Phys. Rev. Lett.*, 38: 771–774 (1977).
Tanaka, T., *Phys. Rev. Lett.*, 40(12): 820–823 (1978).

*Primary Examiner*—Joseph L. Schofer
*Assistant Examiner*—J. M. Reddick
*Attorney, Agent, or Firm*—Hamilton, Brook, Smith & Reynolds

[57] ABSTRACT

Ionized crosslinked polyacrylamide gels are provided that are capable of drastic volume changes in response to minor changes in solvent concentration, temperature of pH or salt concentration of the solvent. The gels can contain a metal ion.

4 Claims, 7 Drawing Sheets

COLLAPSIBLE GEL COMPOSITIONS

The Govenrment has rights in this invention pursuant to grant Number DMR-78-24185 awarded by the National Science Foundation and grant Number NIH-2-RO1-EY01696-04 awarded by the National Institutes of Health.

This application is a continuation of application Ser. No. 06/846,645, filed Mar. 31, 1986 now abandoned, which is a continuation of Ser. No. 06/712,459, filed Mar. 15, 1985 now abandoned, which is a FWC of Ser. No. 06/658,075, filed Oct. 5, 1984, now abandoned which is a continuation of Ser. No. 06/473,161, filed Jan. 28, 1983, now abandoned, designated in PCT Application No. PCT/US81/0073, filed June 8, 1981, the contents ar hereby incorporated by reference.

BACKGROUND OF THE INVENTION

This invention relates to novel gel compositions which are capable of discontinuous volume change of several hundred times induced by infinitesimal changes in environment.

Gel is a form of material between the liquid and solid state. It consists of a crosslinked network of long polymer molecules with liquid molecules trapped within the network. Gels play important roles in various aspects of our everyday life.

In chemistry and biochemistry, gels are used extensively as matrices for chromatography and electrophoresis—analytical methods that separate molecules according to their molecular weights and charges. In these techniques, the pore size of the crosslinked polymer network plays an essential role in its sieving effects.

Gels also are important intermediate products in polymer products such as rubbers, plastics, glues and membranes.

In 1973, a new technique of light scattering spectroscopy was first introduced to gel studies. It was demonstrated that by measuring the intensity and the time dependence of fluctuations of laser light scattered from a gel, it is possible to determine the viscoelastic properties of the gel, that is, the elasticity of the polymer network and the viscous interaction between the network and the gel fluid. Recently, with the help of this powerful technique, very interesting phenomena in permanently crosslinked gels have been found: as the temperature is lowered, the polymer network becomes increasingly compressible, and at a certain temperature it becomes infinitely compressible. At the same time, the effective pore size of the network increases and diverges. It is also observed that the volume of polyacrylamide gels ranges reversibly by a factor as large as several hundred by an infinitesimal change in external conditions such as solvent composition or temperature. Tanaka, Physical Review Letters, Vol. 40, No. 12, pgs. 820–823, 1978 and Tanaka et al., Physical Review Letters, Vol. 38, No. 14, pgs, 771-774, 1977. While these gels can be useful as a switching device or artificial muscle due to their ability to undergo discrete volume changes caused by minute environmental changes, it would be desirable to provide gels which undergo greater volume changes in order to maximize the efficiency of the functions.

SUMMARY OF THE INVENTION

This invention is based upon the discovery that ionized acrylamide gel compositions are capable of more drastic volume change as compared to the acrylamide gel composition of the prior art. The gel compositions comprise a crosslinked partially ionized polyacrylamide gel wherein between up to 20% of the amide groups are hydrolyzed to carboxyl groups. The gel includes a solvent of a critical concentration at which a slight change in temperature, pH or, salt concentration causes the gel to shrink or swell drastically. The particular critical concentration utilized in the gel composition depends upon the solvent employed, the temperature of the gel and the degree of hydrolysis of the gel. The gel also can contain a positive metal ion such as sodium or magnesium which has the effect of increasing the change in gel volume caused by change of solvent concentration, temperature, pH or, salt concentration.

DESCRIPTION OF SPECIFIC EMBODIMENTS

The chemical structure of the network plays as essential role in determining the collapse and other equilibrium behavior of gels. Acrylamide gel consists of linear polymer chains of acrylamide molecules crosslinked by bisacrylamide molecules, which consists of two acrylamide molecules connected together. The interstitial space of the polymer network is filled with water. The gel can be prepared from acrylamide monomers and bisacrylamide monomers that are dissolved in water. Thereafter a polymerization initiator such as ammonium persulfate and TEMED (tetramethyl-ethylenediamine) are added to the solution. First, a reaction between amonium persulfate and TEMED occurs which produces free radical electrons on the TEMED molecules. These molecules of TEMED with free radicals are the nuclei of the polymerization. The free radical on the TEMED molecule attacks and opens one of the double bonded carbon atoms of acrylamide and bisacrylamide monomers. One electron of the acrylamide or bisacrylamide double bond pairs with the odd electron of the free radical to form a bond between the free radical and this carbon atom; the remaining electron of the double bond shifts to the other carbon atom, which then becomes a free radical. In the way, the active center shifts uniquely to the newly added monomer, which then becomes capable of adding another monomer. The acrylamide monomers, having one double bond, are therefore polymerized into a linear chain. The bisacrylamide molecule, consisting of two connected acrylamide molecules have two double bonds and serve as crosslinks. This chain reaction continues until a network consisting of practically an infinite number of bonded monomers if formed. Both polymerization and crosslinking take place almost instantaneously when the first free radical appears. The infinite polymer network is thus formed at this instant.

Figure 1:
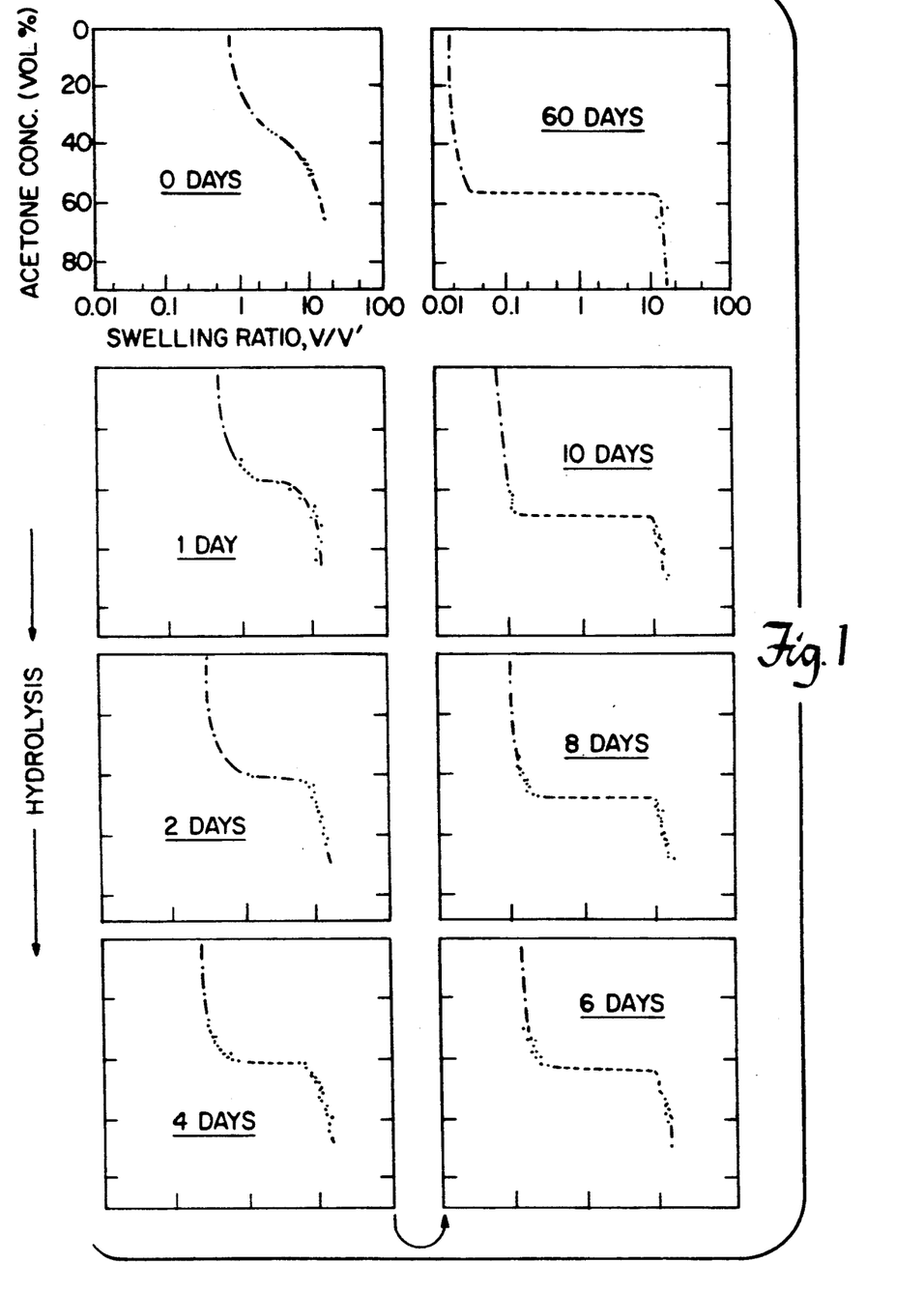
FIG. 1 shows the swelling ratio of polyacrylamide gels as a function of acetone concentration and degree of hydrolysis.

The gels are then taken out of the container. With syringe and needle the gel can be carefully separated from the container wall by forcing water between the gel and the wall. Each gel sample is then soaked in water so that all the residual acrylamide, bisacrylamide monomers and the initiators are washed away. The gels are then immersed in a basic solution of TEMED (4% in volume) having pH of 12 for a time period of up to 60 days. During this immersion period the acrylamide groups of the network, $-COHN_2$ are hydrolyzed into carboxyl groups, $-COOH$, a quarter of which are automatically ionized into carboxyl ions, $-COO^-$, and hydrogen ions, $H^+$. The polymer network becomes negatively charged having positive hydrogen ions, $H^+$, in the interstitial space. The longer the immersion time, the more charges the polymer network becomes. After the hydrolysis the gels are soaked in water to be washed. At this final stage of sample preparation the gel is largely swollen in water. A fully hydrolyzed gel, for example, swells 30 times form the original volume. By this procedure, gel samples having different degrees of ionization can be prepared. Each gel sample then is immersed in a large volume of a solvent such as acetone, acetone and water mixture, ethanol and water, methanol and water. For example, when using a mixture of acetone and water, the water inside the network and the acetone-water mixture outside are exchanged within 30 minutes by diffusion. The equilibrium state, however, is not yet reached. Depending on the acetone concentration, some of the gels shrink. As shown in FIG. 1, the degree of swelling as a function of acetone concentration for various hydrolysis ties at room temperature. The degree of swelling is defined as the ratio of the final volume, V to the original volume $V^+$ of the polymer network when the gel is first polymerized. At low acetone concentration, the gel is swollen. As the acetone concentration is increased, the gel gradually shrinks. The degree of swelling changes continuously with the acetone concentration. For a gel with two days of hydrolysis, the swelling curve shows an inflection point at which the swelling curve has a zero slope. For a gel with 4 days at hydrolysis, the swelling curve has a discrete transition. At low concentrations of acetone, the gel swells. As the acetone concentration increases, the gel shrinks a little; but at 42% acetone concentration of the network suddenly collapses. Above this concentration, the network remains shrunken. This phenomenon is entirely reversible. When a collapsed gel is transferred into a mixture having an acetone concentration lower than 42%, the gel swells until it reaches the network volume indicated by the swelling curve. For gels hydrolyzed longer than 4 days, it can be seen that the size of the collapse becomes larger with hydrolysis. For 60 days of hydrolysis, the volume change at the transition is more than 350 fold. Therefore, by changing the acetone concentration infinitesimally a reversible volume change of several hundred-fold can be effected.

Figure 2:
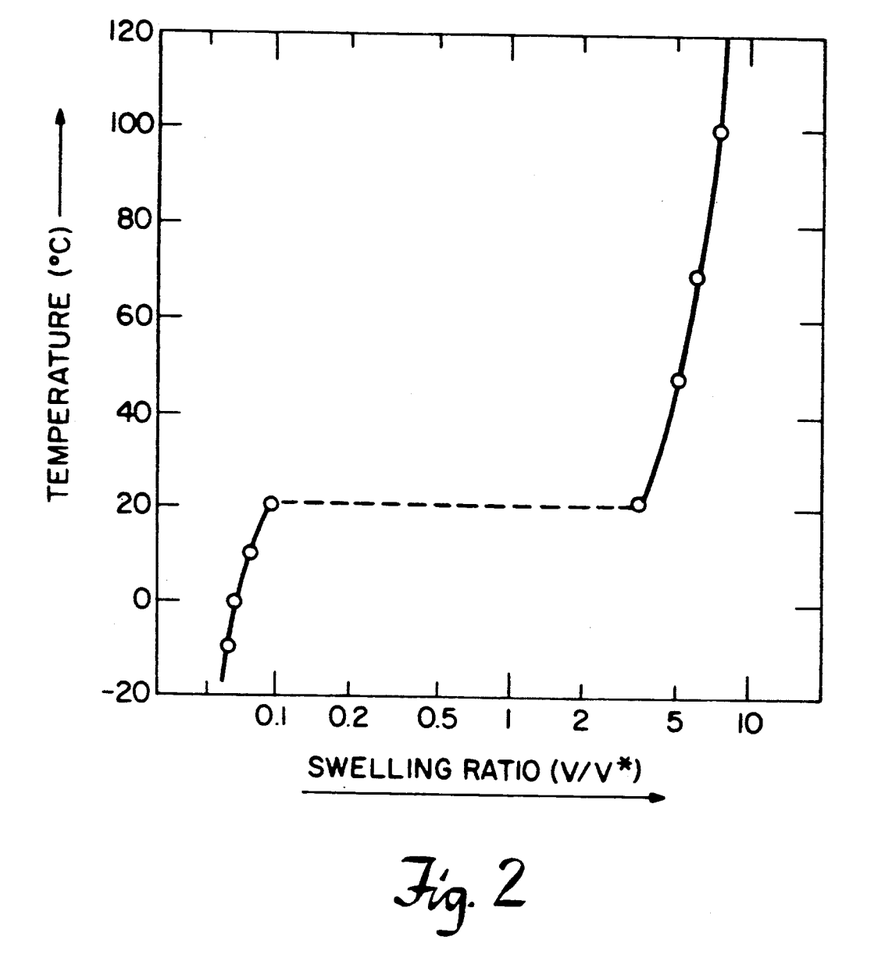
FIG. 2 shows the swelling ratio of a polyacrylamide gel as a function of temperature at a given solvent concentration.

As shown in FIG. 2, the collapse is also observed when for a fixed acetone concentration the temperature is varied. The illustration shows the swelling ratio curve of the gel (hydrolyzed for 8 days) immersed in the mixture of 42% acetone concentration. At temperatures higher than room temperature the network swells, and below it, it shrinks. There is a discontinuous volume change at room temperature.

The total pressure that acts either to expand or to shrink the polymer network of a gel consists of three types of pressures: the rubber elasticity, the polymer-polymer affinity, and the pressure of hydrogen ions. The rubber elasticity is attributed to the elasticity of individual polymer chains constituting the gel network. Consider a single polymer chain consisting of freely joined segments but with both its ends fixed. Due to the random thermal motions of each segment, there are forces which pull the fixed ends. When the polymer is in a compressed configuration, the forces act outward. When the polymer has an extended configuration, on the other hand, the forces act inward. Such forces create the elasticity which acts to keep the polymer chain at a particular degree of expansion at which there are no forces to expand or shrink the polymer chain. The more active the motions of the segments, the stronger the elasticity. The elasticity is therefore proportional to the absolute temperature.

It is essential to take the interactions among polymer segments and solvent molecules into account in order to understand the collapse of the gels. In the acrylamide gels with an acetone-water mixture as the gel fluid, the polymer segments have greater affinity to themselves than to the solvent molecules. Such affinity among polymer segments creates a pressure acting to shrink the network. Such negative pressure is independent of temperature, but does depend on the solvent composition. Since the acrylamide molecules are less soluble in acetone than in water, this negative pressure increases with acetone concentration.

Finally, the ionization produces a positive pressure to expand the network. In the gel the hydrogen ions, $H^+$ are freely moving without experiencing much repulsive force among themselves because the negative charge background of the polymer network shields the electric repulsion. The hydrogen ions, however, cannot leave the network since this would violate the charge neutrality condition in the gel. Thus, the hydrogen ions behave like a gas confined within a small volume and produce a gas type positive pressure. Naturally, this pressure is proportional to the absolute temperature.

The total pressure on a gel network (i.e., the osmotic pressure of a gel) consists, therefore, of a pressure of rubber elasticity, a pressure of polymer-polymer affinity, and a pressure of hydrogen ions. The equilibrium properties of a gel are determined by their balance, which can be varied by changing either the temperature or the solvent composition. This is because the pressures of the rubber elasticity and the hydrogen ions are proportional to the absolute temperature, while the polymer-polymer affinity is not. It is also because the latter depends on the solvent composition whereas the former two do not.

Figure 3:
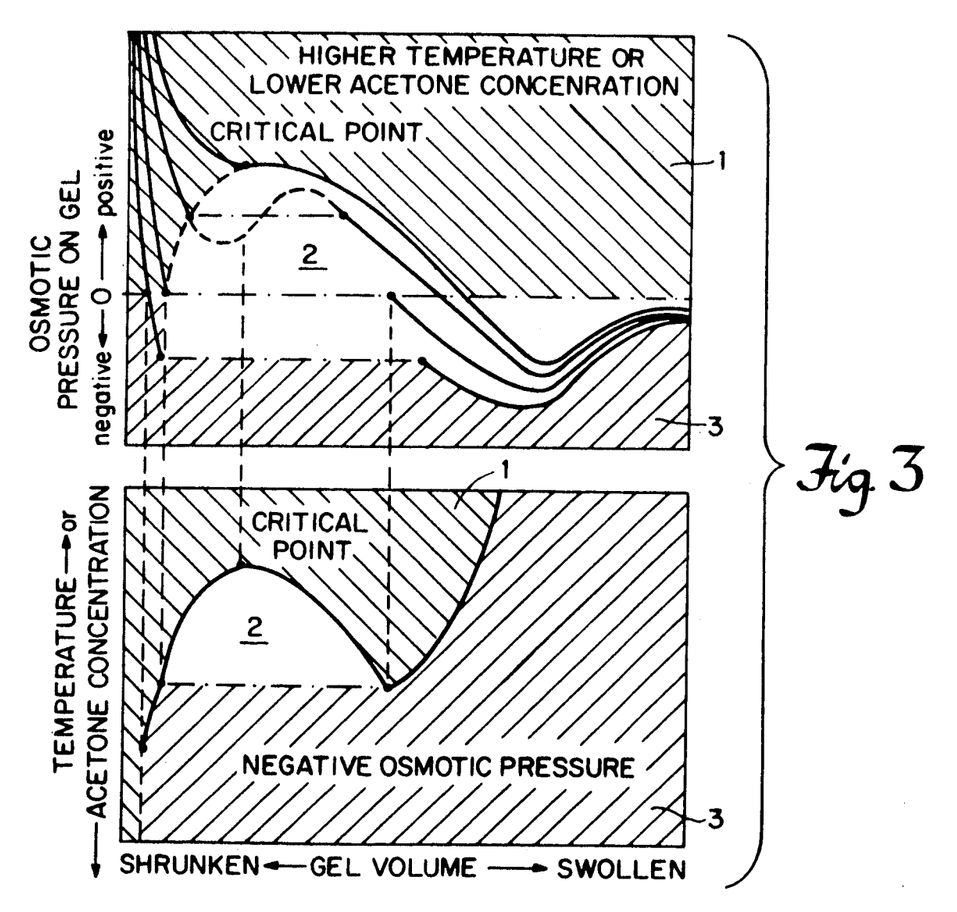
FIG. 3 shows the osmotic pressure of a polyacrylamide gel as a function of the degree of swelling of the gel.

The osmotic pressure of a gel network varies with the degree of swelling at various temperatures, or equivalently, at various acetone concentrations. Such curves of the osmotic pressure vs the degree of swelling are called isotherms. At high temperatures, when a gel is shrunken, its osmotic pressure is positive and the network tends to swell. If a little amount of solvent is added, the gel absorbs it and swells. As the network swells, the osmotic pressure monotonically decreases. At a certain network volume, the osmotic pressure becomes zero, and the gel will not absorb additional solvent. As the temperature is lowered, an isotherm shows an inflection point, then follows a wiggle having a miximum and a minimum. In between these points, the isotherm has a positive slope. This appears because the polymer-polymer affinity becomes more important at lower temperatures and this pressure has a positive slope. Such a positive slope implies a negative compressibility, that is: given more pressure, the network expands. Such a condition is clearly unstable. When thermal agitations cause an infinitesimal local swelling in the network, the osmotic pressure of that region then increases, which leads to further expansion of that region in the network. Therefore, once the local network swelling occurs, it swells further. In the same way, once it starts to shrink locally, it shrinks further. The gel is unstable and separates into two regions, one swollen from the original state and one shrunken. They are shown in FIG. 3 as the two end points of the horizontal line replacing the positive slope. The line is drawn so that it produces equal areas in the loop.

All the elements required for a complete description of the equilibrium properties of the gel are contained in the isotherms. The swelling curve is defined by the condition of zero osmotic pressure, which assures there is equilibrium between the gel and the surrounding fluid. The osmotic pressure is zero at the intercept of each isotherm with the volume axis. The swelling curve is shown in the lower diagram as the boundary. The curve indicates a discrete transition at a temperature at which the horizontal line meets the zero osmotic pressure line. This explains the discrete transition observed by the acrylamide gel.

As shown in FIG. 3 (upper diagram), the osmotic pressure of a gel is plotted as a function of the degree of swelling of the network volume for various temperatures or acetone concentrations. The regions 1 and 2 represent positive osmotic pressure, whereas the region 3 represents negative osmotic pressure. In the region 1, the curves of osmotic pressure have a positive slope, which indicates unstable states for the gel. The gel, then separates into two domains of gels having two different degrees of swelling represented by the end points of the horizontal line which produces two equal areas (shown as shadowed) in the curve. The volume of a gel in equilibrium with the surrounding fluid is achieved at zero osmotic pressure. The zero osmotic pressure is shown as the upper boundary of the region. The discrete transition occurs when the horizontal line in the osmotic pressure curve touches this boundary.

As shown in FIG. 3 (lower diagram), each point in this phase diagram represents a state of a gel. A gel state represented by a point in the region 1 is stable. In the region 2 a gel is unstable and separates into two domains of gels having different degrees of swelling. In the region 3, a gel shrinks until its degree of swelling reaches the boundary of the region 3. On this boundary, the osmotic pressure of a gel is zero; it represents the degree of swelling of a gel in equilibrium with the surrounding fluid.

Two conditions are required for a gel to be stable. First, the osmotic pressure of the gel must be zero or positive. It is negative, the network shrinks excluding the pure fluid. Second, the gel state should be outside the horizontal line. The phase diagram obtained by such consideration is shown in FIG. 3 in the lower graphs of the illustration. The horizontal axis shows the degree of swelling of the network. The vertical axis indicates either temperature or solvent composition. Each point on the graph uniquely defines the state of a gel. The regions indicated by region 3 represent states of a gel having negative osmotic pressures. Gel in this region is unstable and shrinks. In the region 1, a gel is not stable and separates into two regions. Some part of the gel shrinks and some other part swells, and the domain of these two phases coexist. The boundary of this region is, therefore, called the coexistence curve. The two separated gel phases become identical at the maximum of the coexistence curve, and the maximum is called the critical point. A gel having a state represented by a point in the region 1 is stable.

Experimental results show that the volume change at the transition can vary depending on the degree of ionization of the polymer network. The volume change at the transition is observed to range from zero continuous change) to 350 fold.

Figure 4:
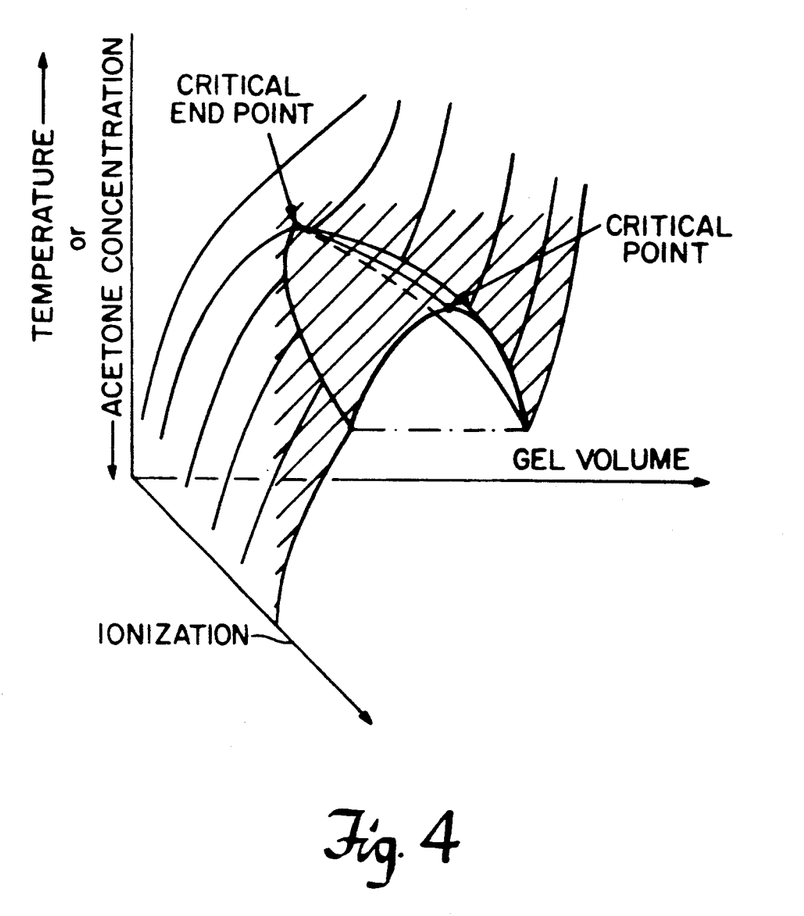
FIG. 4 is a phase diagram of a polyacrylamide gel as a function of degree of ionization and temperature or solvent concentration.

From FIG. 4, it can be seen that the volume change of a gel at the transition is determined by the relative position of the critical point and transition temperature (or solvent composition). If the critical point is well above the transition point, the volume change at the transition is large. As they come closer, the volune change becomes smaller, and eventually it becomes continuous when the critical temperature coincides with the transition temperature. When the polymer network is first polymerized it may be expected that there is no ionization in the network. During immersion in a basic solution the polymer network is gradually ionized. The ionization of the polymer network produces an excess positive pressure due to the hydrogen ions. In order for the collapse to occur, this excess positive pressure must be matched by the excess negative pressure of polymer-polymer affinity. This is achieved either by lowering the temperature or increasing the acetone concentration. The network collapses at lower temperatures or at higher acetone concentrations. The transition point is, therefore, located below the critical point. With less ionization the critical point and the transition point become closer. At a particular degree of ionization they coincide and the swelling curve becomes continuous. For smaller ionization, the critical point becomes buried in the region of negative osmotic pressure. In other words, the critical point becomes unstable and ceases to exist. This final point is called the critical end point for the critical point. Thus, the volume change at the transition is determined by the degree of hydrolysis of the network.

Figure 5:
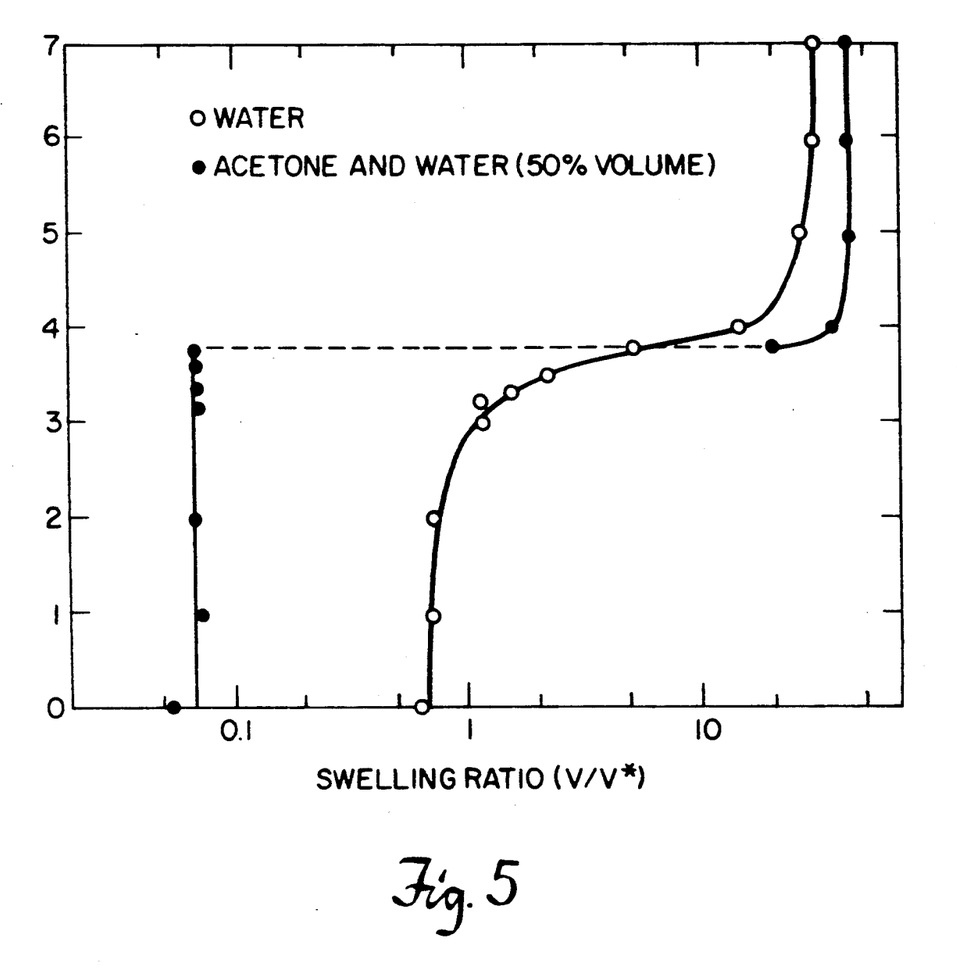
FIG. 5 is a graph of the swelling ratio of polyacrylamide gel as a function of pH.
Figure 6:
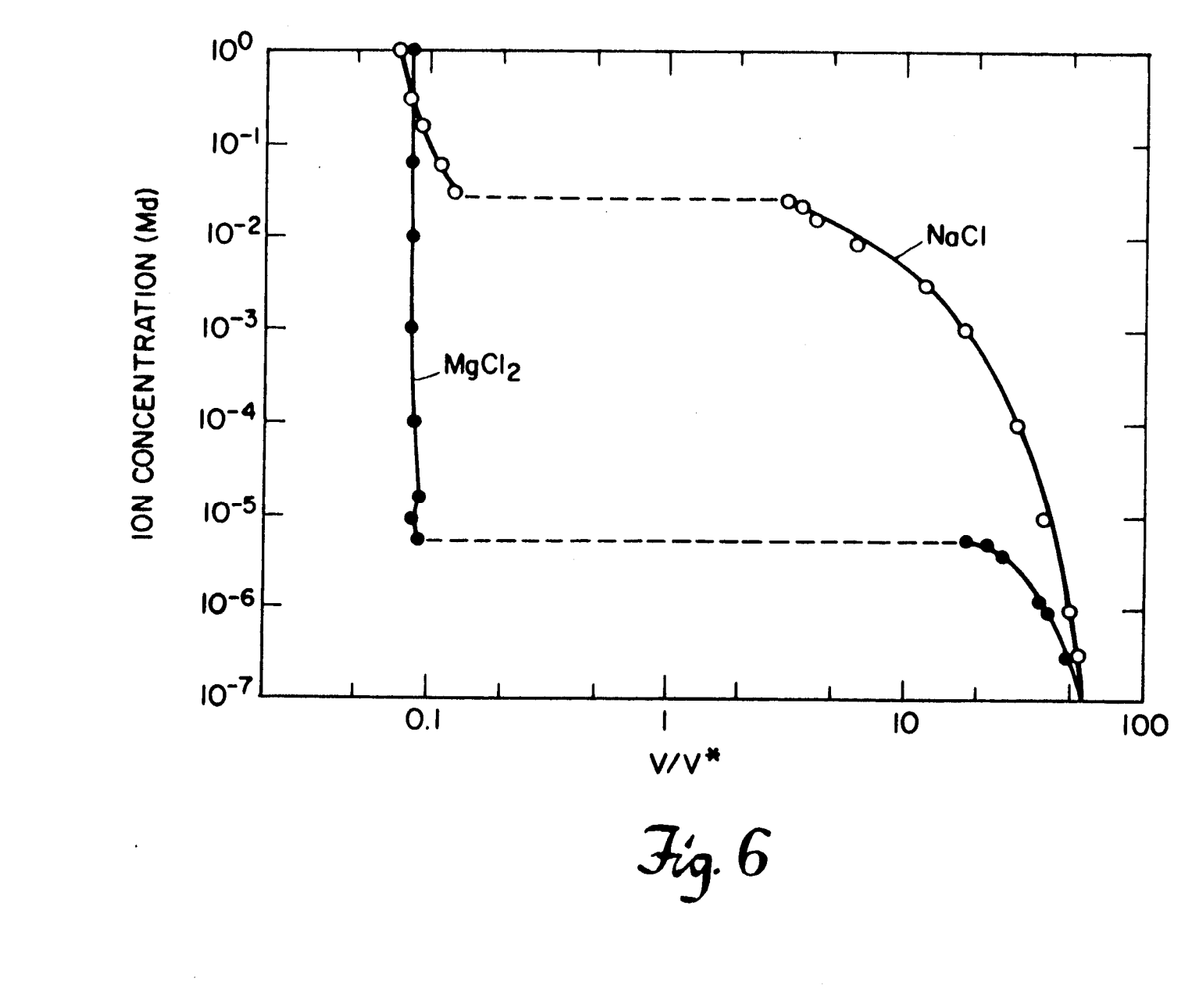
FIG. 6 is a graph showing the effect of sodium ion or magnesium ion concentration on the swelling ratio of a polyacrylamide gel.

A gel collapse also occurs when, for given temperature and acetone concentration, the ionization is changed by varying the pH of the solvent or by adding ions to the solvent. The equilibrium gel volume is given by a intercept line of the zero-osmotic-pressure plane shown in FIG. 4 and the horizontal plane which represents a fixed temperature and acetone concentration. When the horizontal plane is above the critical end point, the intercept is continuous. When the plane is below it, the intercepts has discontinuity. A continuous volume change is observed upon changing the pH, when a solvent with low acetone concentration is used, and a discontinuous curve when a higher acetone concentration is used. As shown in FIG. 5, gel collapse changes with pH of the solvent. The swelling curve shows a continuous change when water is used as a solvent, whereas the swelling curve is discrete when 50% acetone-water mixture is used.

The effective ionization can also be modified by adding metal ions such as by adding salts such as NaCl, KCl, $MgCl_2$, or the like, since the positive ions shield the negative charges of the polymer network. The transition concentration for the divalent ion, $Mg^{++}$, is 4000 times smaller than that for the monovalent ion, $Na^+$. Surprisingly, the large difference can be explained by the fact that only half as many divalent ions are needed to neutralize the network as monovalent ions. It is interesting to note that divalent ions have an essential role in the contraction of muscle, a process that is some respects seems to resemble the collapse of a gel.

Figure 7:
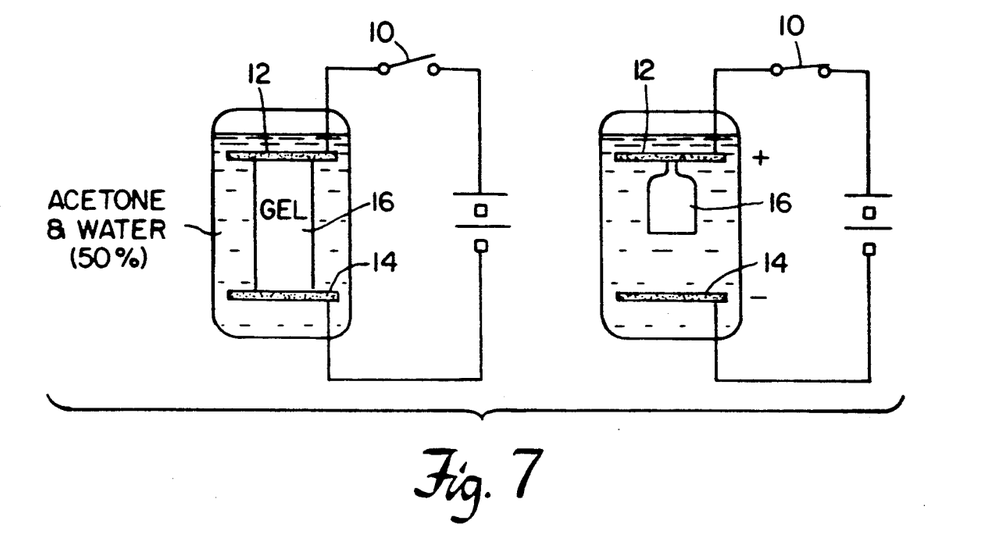
Figure 8:
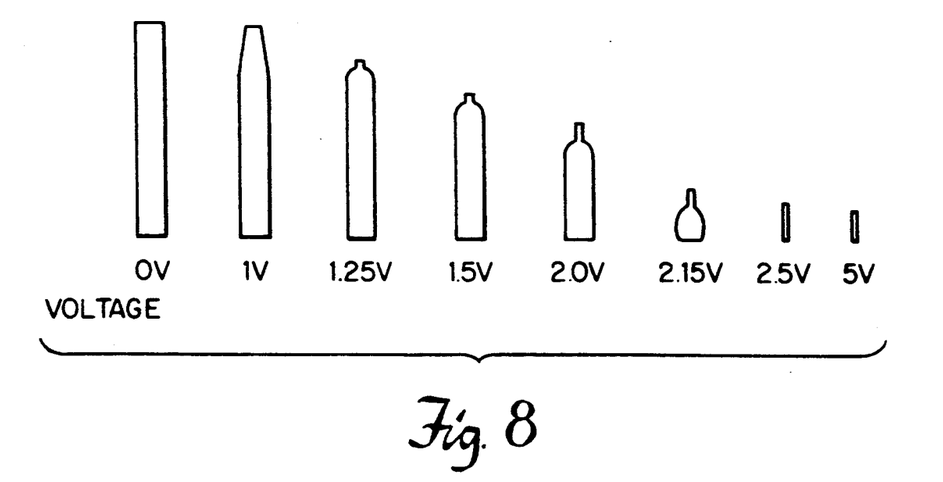

Finally, the transition can be induced by applying an electric filed across the gel in a 50% acetone-water mixture. As shown in FIG. 7, when switch 10 is closed to cause current flow between anode 12 and cathode 14, gel cylinder 16 contracts. When an electric field (~0.5/cm) is applied across the electrodes, the negative charges on the polymer network are pulled toward the positive electrode. This produces a pressure gradient along the electric field. The pressure is strongest on the gel end at the positive electrode and zero at the other end of the gel. There is a critical pressure above which the gel collapses and below which it is swollen. The gel, therefore, has a bottle shape as shown in FIG. 7. As shown in FIG. 8, the swollen portion becomes shorter as the electric field becomes stronger. The collapsed part swells again when the electric field is turned off.

The drastic volume change upon infinitesimal variation of external conditions such as temperature, solvent, and an electric field across the gel may have a variety of applications. Various chemical engines may be designed using gels. A gel having such mechanico-chemical amplification will be useful as an artificial muscle. The time taken for swelling or shrinking is proportional to the square of a linear size of a gel. For example, for a cylindrical gel of 1 cm diameter, it takes several days to reach a new equilibrium volume. For cylindrical gel of 1 μm in diameter, which is the size of muscle filament, it would take only a few thousandths of a second. This is quick enough to be used as an artificial muscle. The discrete change in volume of a gel may be used as a mechanico-chemical memory or a switch.

We claim:

1. A method of causing a discontinuous volume change in a gel, said gel including a polymer network defining an interstitial space and a gel fluid filling the interstitial space, comprising the steps of:
    a) ionizing the gel sufficient to cause the gel to exhibit a discontinuous volume change upon exposure to sufficient electromagnetic radiation; and
    b) exposing the gel to electromagnetic radiation sufficient to cause the gel to exhibit a discontinuous volume change.

2. A method of claim 1 wherein the electromagnetic radiation is supplied by conducting an electric current through the gel.

3. A method of causing a discontinuous volume change in a gel, said gel including a polymer network defining an interstitial space and a gel fluid filling the interstitial space, comprising the steps of:
    a) ionizing the gel sufficient to cause the gel to exhibit a discontinuous volume change upon exposure to metal ions; and
    b) exposing the gel to metal ions, whereby the gel exhibits a discontinuous volume change.

4. A method of causing a discontinuous volume change in a gel, said gel including a polymer network defining an interstitial space, a concentration of metal ions dispersed within the interstitial space and a gel fluid filling the interstitial space, comprising the steps of:
    a) ionizing the gel sufficient to cause the gel to exhibit a discontinuous volume change upon sufficiently changing the metal ion concentration to which the gel is exposed to cause the gel to exhibit a discontinuous volume change; and
    b) changing the metal ion concentration to which the gel is exposed sufficient to cause the gel to exhibit a discontinuous volume change.

* * * * *